(12) United States Patent
Miyahara

(10) Patent No.: US 11,647,970 B2
(45) Date of Patent: May 16, 2023

(54) NUCLEAR MEDICINE DIAGNOSIS APPARATUS

(71) Applicant: CANON MEDICAL SYSTEMS CORPORATION, Tochigi (JP)

(72) Inventor: Masaki Miyahara, Otawara (JP)

(73) Assignee: CANON MEDICAL SYSTEMS CORPORATION, Tochigi (JP)

(*) Notice: Subject to any disclaimer, the term of this patent is extended or adjusted under 35 U.S.C. 154(b) by 0 days.

(21) Appl. No.: 17/469,754

(22) Filed: Sep. 8, 2021

(65) Prior Publication Data

US 2022/0071575 A1  Mar. 10, 2022

(30) Foreign Application Priority Data

Sep. 8, 2020 (JP) .............................. JP2020-150697

(51) Int. Cl.
| | | |
|---|---|---|
| *G01T 1/202* | (2006.01) | |
| *G01T 1/20* | (2006.01) | |
| *A61B 6/03* | (2006.01) | |
| *A61B 6/00* | (2006.01) | |

(52) U.S. Cl.
CPC ............ *A61B 6/037* (2013.01); *A61B 6/4258* (2013.01); *G01T 1/202* (2013.01); *G01T 1/2006* (2013.01)

(58) Field of Classification Search
CPC ....... A61B 6/037; A61B 6/4258; A61B 6/585; G01T 1/2006; G01T 1/202; G01T 1/1647; G01T 1/2985
See application file for complete search history.

(56) References Cited

U.S. PATENT DOCUMENTS

| | | | | |
|---|---|---|---|---|
| 6,362,479 B1 * | 3/2002 | Andreaco | ............ | G01T 1/1644 |
| | | | | 250/363.01 |
| 7,202,477 B2 * | 4/2007 | Srivastava | ............ | G01T 1/2023 |
| | | | | 250/361 R |
| 7,405,404 B1 * | 7/2008 | Shah | .................. | C09K 11/7719 |
| | | | | 250/361 R |
| 7,723,687 B2 * | 5/2010 | Nagarkar | ................ | G01T 1/202 |
| | | | | 250/361 R |
| 9,063,087 B2 * | 6/2015 | Tsuda | .................... | G01T 1/1644 |
| 9,360,569 B2 * | 6/2016 | Tsuda | ...................... | G01T 1/208 |
| 9,599,743 B2 * | 3/2017 | Inanc | ....................... | G01N 9/24 |
| 9,844,351 B2 * | 12/2017 | Tsuda | ...................... | G01T 1/208 |
| 9,921,161 B1 * | 3/2018 | Feldkhun | ............ | G01N 21/6458 |
| 10,234,577 B2 * | 3/2019 | Joung | ..................... | G01T 7/005 |
| 10,247,931 B2 * | 4/2019 | Sirat | ....................... | G02B 21/16 |
| 10,436,915 B2 * | 10/2019 | Teshigawara | .......... | A61B 6/037 |

(Continued)

*Primary Examiner* — David P Porta
*Assistant Examiner* — Djura Malevic
(74) *Attorney, Agent, or Firm* — Oblon, McClelland, Maier & Neustadt, L.L.P.

(57) ABSTRACT

A nuclear medicine diagnosis apparatus according to an embodiment includes a scintillator configured to emit self-radiation, storage, and processing circuitry. The storage stores first detection efficiency correction data that is generated based on an external radiation source or a simulation and first detection efficiency data per scintillator that is calculated based on radiation that is emitted from the scintillator. The processing circuitry calculates second detection efficiency data per scintillator that is calculated based on radiation that is emitted from the scintillator and generates second detection efficiency correction data based on the first detection efficiency correction data, the first detection efficiency data, and the second detection efficiency data.

7 Claims, 4 Drawing Sheets

(56) References Cited

U.S. PATENT DOCUMENTS

| | | | |
|---|---|---|---|
| 10,527,741 B2* | 1/2020 | Cho | G01T 1/2985 |
| 10,578,750 B2* | 3/2020 | Ishikawa | C09K 11/7704 |
| 10,775,520 B2* | 9/2020 | Cho | G01T 7/005 |
| 10,831,010 B2* | 11/2020 | Sirat | G02B 21/0072 |
| 2004/0227091 A1* | 11/2004 | LeBlanc | G01T 1/1642 |
| | | | 250/366 |
| 2005/0242288 A1* | 11/2005 | Wollenweber | G01T 1/2985 |
| | | | 250/369 |
| 2009/0008561 A1* | 1/2009 | Nagarkar | G01T 1/202 |
| | | | 250/361 R |
| 2009/0097613 A1* | 4/2009 | Tonami | G01T 1/40 |
| | | | 378/19 |
| 2010/0223010 A1* | 9/2010 | Nikitin | G01V 5/107 |
| | | | 702/8 |
| 2013/0062526 A1* | 3/2013 | Tsuda | G01T 1/2018 |
| | | | 250/362 |
| 2015/0041661 A1* | 2/2015 | Tsuda | G01T 1/1644 |
| | | | 250/361 C |
| 2015/0212308 A1* | 7/2015 | Sirat | G01N 21/6458 |
| | | | 250/459.1 |
| 2016/0242706 A1* | 8/2016 | Tsuda | G01T 1/208 |
| 2016/0299240 A1* | 10/2016 | Cho | G01T 7/005 |
| 2016/0299246 A1* | 10/2016 | Minto | G01V 1/44 |
| 2016/0320523 A1* | 11/2016 | Inanc | G01V 5/12 |
| 2017/0322406 A1* | 11/2017 | Sirat | G02B 21/16 |
| 2018/0149760 A1* | 5/2018 | Ishikawa | G01T 1/17 |
| 2018/0149763 A1* | 5/2018 | Joung | G01T 1/203 |
| 2019/0086557 A1* | 3/2019 | Teshigawara | A61B 6/037 |
| 2019/0324254 A1* | 10/2019 | Sirat | G02B 21/0072 |
| 2020/0072988 A1* | 3/2020 | Cho | G01T 7/005 |
| 2020/0379133 A1* | 12/2020 | Burr | G01T 7/005 |
| 2021/0208293 A1* | 7/2021 | Qi | G01T 1/2985 |
| 2022/0003609 A1* | 1/2022 | Derzon | G01J 5/025 |

* cited by examiner

NUCLEAR MEDICINE DIAGNOSIS APPARATUS

CROSS-REFERENCE TO RELATED APPLICATIONS

This application is based upon and claims the benefit of priority from Japanese Patent Application No. 2020-150697, filed on Sep. 8, 2020; the entire contents of which are incorporated herein by reference.

FIELD

Embodiments disclosed herein relate to a nuclear medicine diagnosis apparatus.

BACKGROUND

Calibration of PET apparatuses includes steps of measuring detection efficiency per scintillator (crystal) and generating data for correction that is used to generate a clinical image, which are steps commonly referred to and known as normalization. In general, normalization is performed by collecting gamma rays from a radiation source for calibration that is arranged in a gantry.

When normalization is performed with a radiation source for calibration, worker radiation exposure may occur in association with handling of the radiation source for calibration. Furthermore, variation in position in which the radiation source is set and variation in accuracy due to non-uniformity of distribution of isotopes in the radiation source may occur.

DETAILED DESCRIPTION

A nuclear medicine diagnosis apparatus that is provided in one aspect of the disclosure includes a scintillator that emits self-radiation, storage, and processing circuitry. The storage stores first detection efficiency correction data that is generated based on an external radiation source or a simulation and first detection efficiency data per scintillator that is calculated based on radiation emitted from the scintillator. The processing circuitry calculates second detection efficiency data per scintillator that is calculated based on radiation emitted from the scintillator and generates second detection efficiency correction data based on the first detection efficiency correction data, the first detection efficiency data, and the second detection efficiency data.

With reference to the drawings, an embodiment of the nuclear medicine diagnosis apparatus will be described in detail below.

Figure 1:
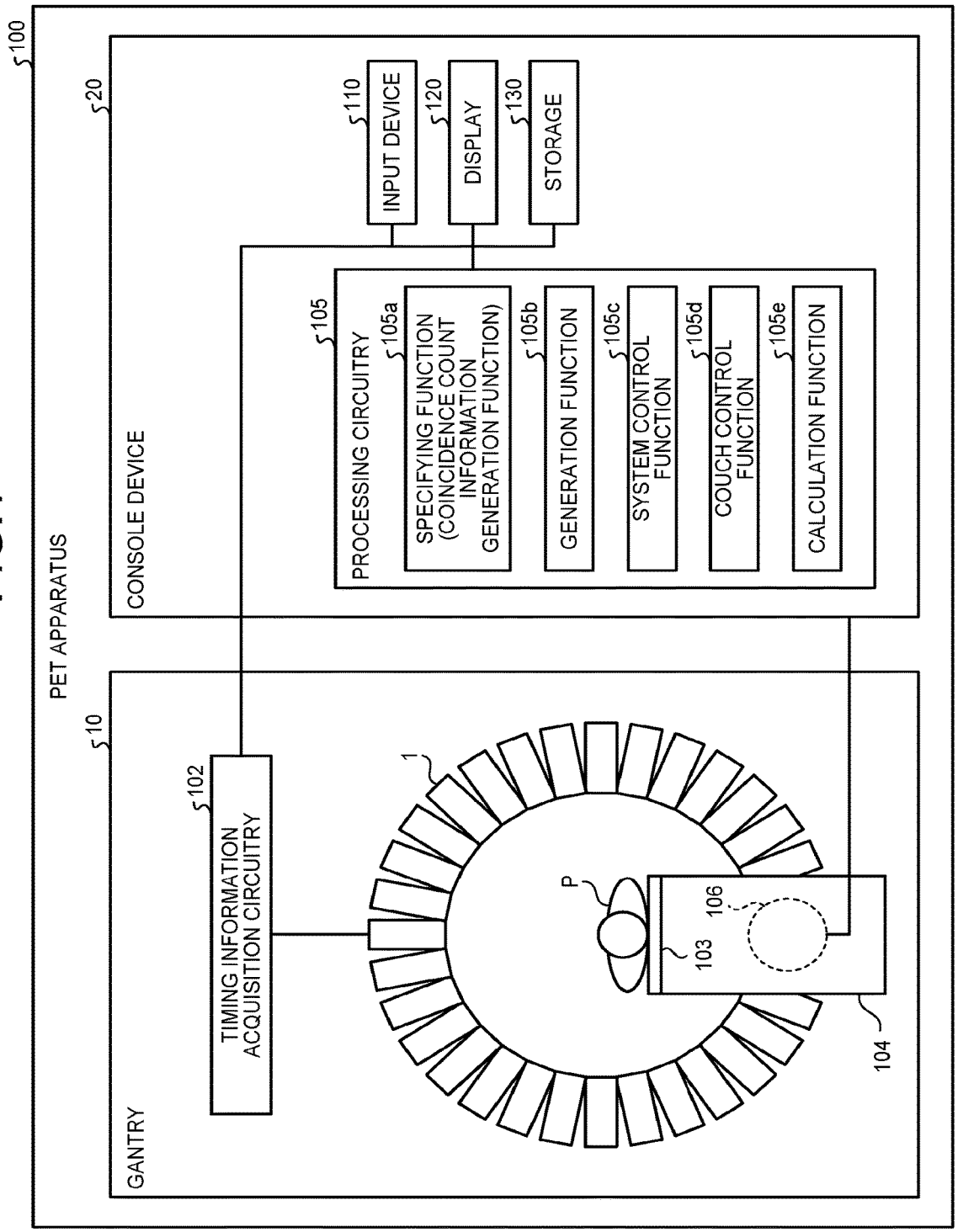
FIG. 1 is a diagram illustrating a configuration of a nuclear medicine diagnosis apparatus according to an embodiment.

FIG. 1 is a diagram illustrating a configuration of a PET apparatus 100 according to the embodiment. As illustrated in FIG. 1, the PET apparatus 100 according to the embodiment includes a gantry 10 and a console device 20.

The gantry 10 includes a detector 1, timing information acquisition circuitry 102, a couchtop 103, a couch 104, and a couch driver 106

The detector 1 is a detector that detects radiation by detecting scintillation light (fluorescent light) that is light re-emitted when a substance that had become an excited state because annihilation gamma rays emitted from positrons in a subject P interact with an illuminant (scintillator) shifts to a ground state again. The detector 1 detects energy information on radiation of annihilation gamma rays that are emitted from positrons in the subject P. A plurality of the detectors 1 are arranged such that the detectors 1 surround the subject P in a form of a ring and the detector 1 consists of a plurality of detector blocks.

An example of a specific configuration of the detector 1 is a photon counting detector of an anger type including, for example, a scintillator, a light detection element, and a light guide. In other words, each pixel contained in the detector 1 includes a scintillator and a light detection element that detects generated scintillation light.

The scintillators convert annihilation gamma rays that are emitted from positrons in the subject P and are incident on the scintillators into scintillation light (scintillation photons or optical photons) and output the scintillation light. The scintillators are formed of scintillator crystals of LaBr3 (Lanthanum Bromide), LYSO (Lutetium Yttrium Oxyorthosilicate), LSO (Lutetium Oxyorthosilicate), LGSO (Lutetium Gadolinium Oxyorthosilicate), BGO, or the like, that are suitable for TOF measurement and energy measurement and the scintillator crystals are, for example, arrayed two-dimensionally. The scintillators of which the detector 1 consists emit self-radiation. In one example, the scintillators of which the detector 1 consists contain $^{176}$Lu that is radionuclides and emit gamma rays that are emitted from that $^{176}$Lu as self-radiation.

For example, a SiPM (Silicon photomultiplier) or a photomultiplier tube is used as the light detection element. The photomultiplier tube includes a photocathode that receives scintillation light and generates photoelectrons, multiple stages of dynode that provide an electric field that accelerates the generated photoelectrons, and an anode serving as an electron flow outlet and the photomultiplier multiplies the scintillation light that is output from the scintillator and converts the multiplied scintillation light into an electric signal.

Using the timing information acquisition circuitry 102, the gantry 10 generates count information from an output signal from the detector 1 and stores the generated count information in storage 130 of the console device 20. The detector 1 is divided into multiple blocks and includes the timing information acquisition circuitry 102.

The timing information acquisition circuitry 102 converts the output signal from the detector 1 into digital data and generates count information. The count information contains a position of detection of annihilation gamma rays, an energy value, and a time of detection. For example, the timing information acquisition circuitry 102 specifies a plurality of light detection elements that convert scintillation light into electric signals at the same timing. The timing information acquisition circuitry 102 then specifies scintillator numbers (P) each indicating a position of a scintillator into which annihilation gamma rays are incident. The unit that specifies a position of a scintillator on which annihilation gamma rays are incident may specify a scintillation position by performing a center-of-gravity operation based on the position of each light detection element and the intensity of electric signal. When each scintillator and each light detection element coincides in element size, a scintillator corresponding to a light detection element of which output is obtained may be specified as a position of a scintillator on which annihilation gamma rays are incident.

The timing information acquisition circuitry 102 specifies an energy value (E) of annihilation gamma rays that are incident on the detector 1 by performing an integration on the intensities of electric signals that are output from the respective light detection elements. The timing information acquisition circuitry 102 specifies a detection time (T) at which the detector 1 detects scintillation light caused by annihilation gamma rays. The detection time (T) may be an absolute time or may be an elapse of time from the time of start of imaging. As described above, the timing information acquisition circuitry 102 generates count information containing scintillator numbers (P), an energy value (E), and a detection time (T).

The timing information acquisition circuitry 102 is realized using, for example, a CPU (Central Processing Unit), a GPU (Graphical Processing Unit), or a circuit, such as an application specific integrated circuit (ASIC), a programmable logic device (for example, a simple programmable logic device (SPLD)), a complex programmable logic device (CPLD), or a field programmable gate array (FPGA). The timing information acquisition circuitry 102 is an example of a timing information acquisition unit.

The couchtop 103 is a bed on which the subject P is laid and is arranged on the couch 104. The couch driver 106 shifts the couchtop 103 under the control of a couch control function 105d of the processing circuitry 105. For example, the couch driver 106 shifts the couchtop 103, thereby shifting the subject P to an imaging port of the gantry 10.

The console device 20 receives an operation of an operator on the PET apparatus 100 and controls capturing of a PET image and reconstructs a PET image using count information that is collected by the gantry 10. As illustrated in FIG. 1, the console device 20 includes the processing circuitry 105, an input device 110, a display 120, and the storage 130. The units that the console device 20 includes are connected with one another via a bus.

In the embodiment, each of processing functions that are performed by a specifying function (coincidence count information generation function) 105a, a generation function 105b, a system control function 105c, the couch control function 105d, and a calculation function 105e is stored in a form of a computer-executable program in the storage 130. The processing circuitry 105 is a processor that reads the programs from the storage 130 and executes the programs, thereby implementing the functions corresponding to the respective programs. In other words, the processing circuitry 105 having read the respective programs have the respective functions illustrated in the processing circuitry 105 in FIG. 1. As for FIG. 1, the single processing circuitry 105 is described as one that implements the processing functions performed by the specifying function (coincidence count information generation function) 105a, the generation function 105b, the system control function 105c, the couch control function 105d, and the calculation function 105e; however, multiple independent processors may be combined to configure the processing circuitry 105 and the respective processors may execute the respective programs, thereby implementing the functions. In other words, each of the programs is configured as a program and the single processing circuitry 105 may execute each of the programs. In another example, a specific function may be installed in a dedicated and independent program execution circuit.

Note that, in FIG. 1, the specifying function 105a, the generation function 105b, the system control function 105c, the couch control function 105d, and the calculation function 105e are examples of a specifying unit, a generation unit, a system control unit, a couch control unit, and a calculation unit.

The term "processor" used in the description above means, for example, a CPU (Central Processing Unit), a GPU (Graphical Processing Unit), or a circuit, such as an application specific integrated circuit (ASIC), a programmable logic device (for example, a simple programmable logic device (SPLD)), a complex programmable logic device (CPLD), or a field programmable gate array (FPGA). The processor reads the programs that are saved in the storage 130 and executes the programs, thereby implementing the functions.

By the specifying function (coincidence count information generation function) 105a, the processing circuitry 105 generates coincidence count information based on the count information on the detector 1 that is acquired by the timing information acquisition circuitry 102 and stores the generated coincidence count information in the storage 130.

By the generation function 105b, the processing circuitry 105 reconstructs a PET image. Specifically, by the generation function 105b, the processing circuitry 105 reads a time-series list of sets of coincidence count information that is stored in the storage 130 and reconstructs a PET image using the read time-series list. The processing circuitry 105 stores the reconstructed PET image in the storage 130.

By the system control function 105c, the processing circuitry 105 controls the gantry 10 and the console device 20, thereby generally controlling the PET apparatus 100. For example, by the system control function 105c, the processing circuitry 105 controls imaging in the PET apparatus 100.

By the couch control function 105d, the processing circuitry 105 controls the couch driver 106.

The input device 110 is a mouse, a keyboard, or the like, that is used by the operator of the PET apparatus 100 to input various instructions and various settings and the input device 110 transfers various instructions and various settings that are input to the processing circuitry 105. For example, the input device 110 is used to input imaging start instructions.

The display 120 is a monitor, or the like, that is referred to by the operator and, under the control of the processing circuitry 105, displays a respiratory waveform or a PET image of the subject or display a GUI (Graphical User Interface) for receiving various instructions and various settings from the operator.

The storage 130 stores various types of data that are used in the PET apparatus 100. The storage 130 consists of, for example, a memory and, in one example, is realized using a semiconductor memory device, such as a RAM (Random Access Memory) or a flash memory, a hard disk, an optical disk, or the like. The storage 130 stores the count information that is information in which scintillator numbers (P), an energy value (E) and a detection time (T) are associated with one another, coincidence count information in which a group of sets of count information is associated with a coincidence NO. that is a serial number of the coincidence count information, and a reconstructed PET.

Figure 2:
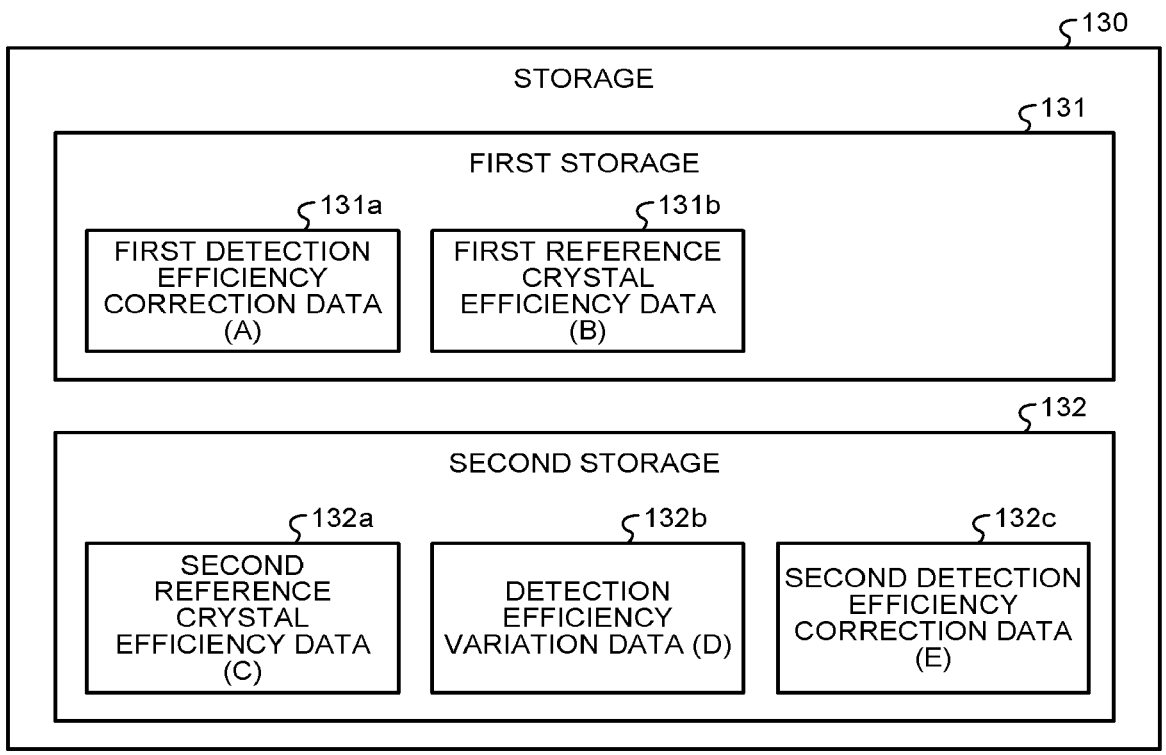
FIG. 2 is a diagram illustrating a configuration of storage of the nuclear medicine diagnosis apparatus according to the embodiment.

As illustrated in FIG. 2, the storage 130 consists of first storage 131 for storing data on normalization at the time of manufacturing or factory shipping and second storage 132 for storing data on normalization that is performed when the apparatus is used in a medical setting. The first storage 131 stores first detection efficiency correction data 131a and a first reference crystal efficiency data 131b to be described below. The second storage 132 stores second reference crystal efficiency data 132a, detection efficiency variation data 132b, and second detection efficiency correction data 132c to be described below.

The background of the embodiment will be described.

Calibration of PET apparatuses includes steps of measuring a detection efficiency per scintillator (crystal) and generating data for correction that is used to generate a clinical image, which are steps commonly referred to and known as normalization. In general, normalization is performed by collecting gamma rays from a radiation source for calibration that is arranged in a gantry.

When normalization is performed using a radiation source for calibration, worker radiation exposure may occur in association with handling of the radiation source for calibration. For example, when the position in which the radiation source is set is adjusted, the time during which the distance between a worker and a radiation source is small tends to be relatively long and thus worker radiation exposure may occur during setting or removal of the radiation source or preparation of a phantom, or the like.

Furthermore, variation in position in which the radiation source is set and variation in accuracy due to non-uniformity in distribution of isotopes in the radiation source may occur.

For example, when a radiation source is set in a gantry, variation may occur depending on positioning accuracy. When normalization is performed with an incorrect phantom setting position, there is a risk that incorrect correction data would be generated. When a non-sealed radiation source, such as a FDG, is used, homogeneity of the radiation source may be insufficient due to an operational error, such as insufficient stirring, and, in the case of a sealed radiation source, homogeneity of a radiation source that is shipped from a radiation source vender may be insufficient.

Thus, in view of the background, in the nuclear medicine diagnosis apparatus according to the embodiment, a detection efficiency per scintillator is calculated based on self-radiation from the scintillator, for example, radiation of $^{176}$Lu. This makes it possible to reduce worker radiation exposure, keep homogeneity of a radiation source, and increase accuracy of normalization.

The configuration will be described using FIGS. 3 to 7. The PET apparatus according to the embodiment measures a detection efficiency per crystal using gamma rays from self-radionuclides contained in the scintillator and compares the measured detection efficiency per crystal with reference data or a history, thereby sensing a change in detection performance of the detector 1 of the PET apparatus 100 over time and a detection function abnormality.

Figure 3:
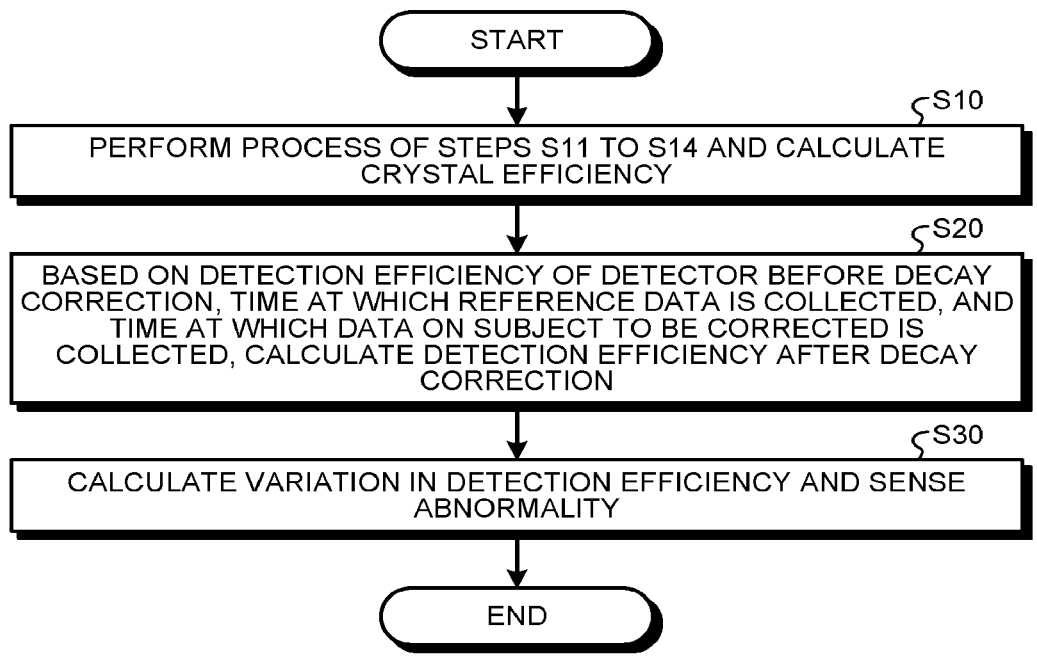
FIG. 3 is a flowchart illustrating a flow of a process that is performed by the nuclear medicine diagnosis apparatus according to the embodiment.
Figure 4:
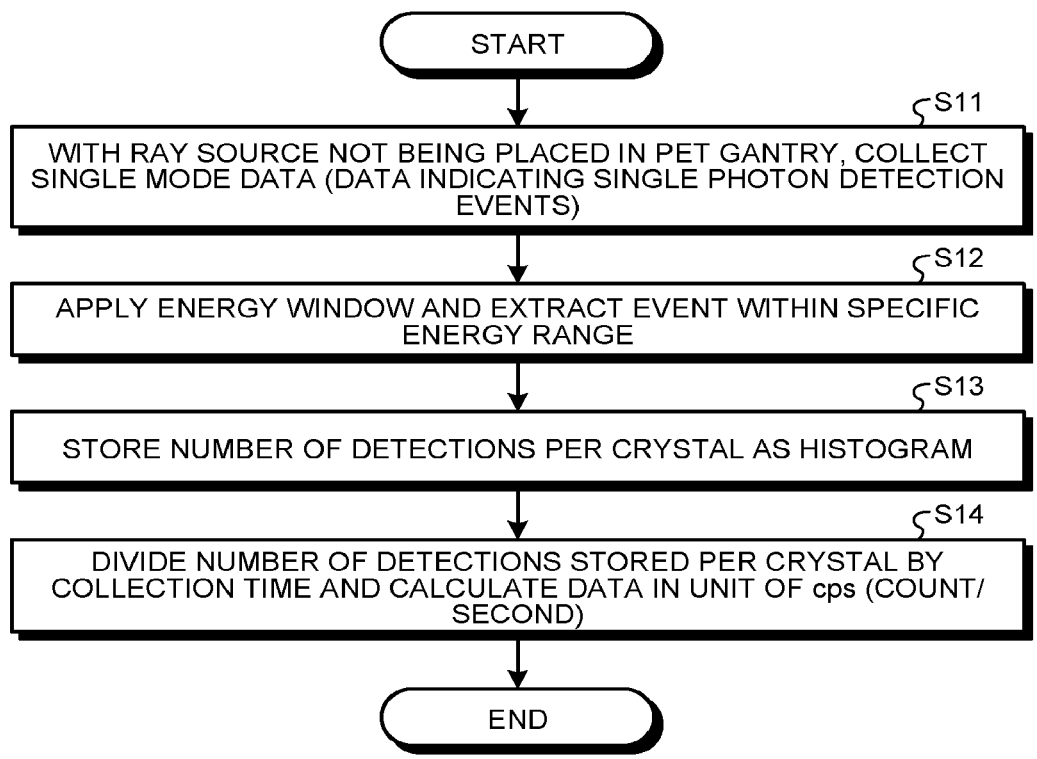
FIG. 4 is a flowchart illustrating a process of step S10 in FIG. 3 more in detail.

First of all, the case where a change in detection performance of the detector 1 over time and a detection function abnormality are detected using data on a gamma ray event in single mode data from the self-radiation in the scintillator will be described. The configuration will be described using FIGS. 3 and 4. FIG. 3 illustrates a general flow of the process and FIG. 4 illustrates the process of step S10 in FIG. 3 in detail.

First of all, in FIG. 3, at step S10, by the calculation function 105e, the processing circuitry 105 measures a detection efficiency per crystal using gamma rays from self-radionuclide contained in the scintillators. Using FIG. 4, the process will be described. FIG. 4 illustrates step S10 in FIG. 3 more in detail. In other words, steps S11 to S14 in FIG. 4 correspond to step S10 in FIG. 3.

First of all, at step S11, the timing information acquisition circuitry 102 collect data of single mode data with the radiation source not being placed in a PET gantry and, for example, collect data on gamma rays from self-radionuclides contained in a scintillator. The single mode data is data representing a single photon detection event and has information of the position of the detection element, the energy and the detection time. By the calculation function 105e, the processing circuitry 105 acquires the collected single mode data from the timing information acquisition circuitry 102.

For example, lutetium nuclides are taken as self-radiation contained in the scintillators.

For example, the scintillators of the nuclear medicine diagnosis apparatus of the embodiment emit gamma rays that are radiated from $^{176}$Lu as radiation by self-radiation contained in the scintillators.

Subsequently, at step S12, by the calculation function 105e, the processing circuitry 105 applies an energy window to the single mode data that is acquired at step S11 and extracts an event in a specific energy range. Specifically, in order to remove circuit noise, scattering photons, and coincidence detection (pile-up) of multiple photons, by the calculation function 105e, the processing circuitry 105, for example, uses an energy window by which only events in the specific energy range are detected, thereby extracting only events in the specific energy range. In one example, when $^{176}$Lu is used as self-radiation, $^{176}$Lu emits gamma rays of 88, 202, 307 and 401 keV and, because 202 keV and 307 keV are dominant, by the calculation function 105e, the processing circuitry 105 applies an energy window of, for example, 180 to 330 keV and thus extracts gamma rays of energy of, for example, 180 to 330 keV and discards others.

At step S13, by the calculation function 105e, the processing circuitry 105 stores the number of detections of events that are extracted at step S12 with respect to each crystal of which the detector 1 consists. In one example, by the calculation function 105e, the processing circuitry 105 stores, as a histogram, the number of detections of events that are extracted at step S12 with respect to each crystal of which the detector 1 consists. At step S13, the storage 130 may store the number of detections of events that are extracted with respect to each crystal in the first storage 131 or the second storage 132.

Subsequently, at step S14, by the calculation function 105e, the processing circuitry 105 divides the number of detections [count] that is stored per crystal at step S13 by a duration of collection [seconds] and calculates data of a unit of count/second [cps].

As described above, by the calculation function 105e, the processing circuitry 105 calculates a detection efficiency per scintillator based on radiation emitted from the scintillator.

Back to FIG. 3, at step S20, by the calculation function 105e, the processing circuitry 105 calculates a detection efficiency of the detector before decay correction, a time at which reference data is collected, and a time at which data to be corrected is collected. In other words, because self-radiation of the detector decreases as the radioactive substance decays and the time passes, the self-radiation reduces as the time passes. By the calculation function 105e, the processing circuitry 105 corrects the effect. For example, by the calculation function 105e, the processing circuitry 105 calculates a detection efficiency after decay correction according to the following Equation (1):

$$R_{corr,p} = R_{measured,p} \cdot \exp\left[\ln 2 \cdot \frac{(T_1 - T_0)}{H}\right] \quad (1)$$

where p denotes a number of a detector, $R_{corr,p}$ denotes a detection efficiency after decay correction by the detector p, $R_{measure,p}$ denotes a detection efficiency (crystal efficiency) before decay correction by the detector p, $T_0$ denotes a time at which reference data is collected, $T_1$ denotes a time at which new data is collected, that is, a time at which single mode data is collected at step S11, and H denote a half-life of self-radioisotope contained in the scintillator. The time at which reference data is collected is, for example the time at which data is collected at the time of factory shipping.

When the half-time of the self-radioisotopes is long, the process of the step can be omitted. For example, because the half-time of $^{176}$Lu is long, $3.78 \ast 10^{10}$ years, the step may be omitted when normalization is performed using self-radiation of $^{176}$Lu.

At step S30, by the calculation function 105e, the processing circuitry 105 compares the detection efficiency after decay correction that is calculated at step S20 with existing data serving as reference data, calculates a variation in the crystal efficiency, and senses an abnormality based on the calculated variation in the crystal efficiency. In other words, by the calculation function 105e, the processing circuitry 105 calculates a variation in the crystal efficiency based on the radiation from the scintillator and, based on the calculated variation in the crystal efficiency, performs an abnormality sensing process.

In one example, by the calculation function 105e, the processing circuitry 105 makes a comparison with the existing data and determines an element without signal output as an abnormal element, thereby sensing an abnormality.

In another example, by the calculation function 105e, the processing circuitry 105 divides the detection efficiency that is calculated at step S20 by the existing data with respect to each element and calculates a variation rate of the detection efficiency and, based on the calculated variation rate, senses an abnormality.

For example, by the calculation function 105e, based on the calculated variation rate of the detection efficiency, the processing circuitry 105 detects an abnormality in the system of the overall apparatus or an abnormality in specific hardware. For example, by the calculation function 105e, the processing circuitry 105 determines that a system abnormality occurs over the apparatus when the calculated variation rate of the detection efficiency exceeds a threshold over the detector, for example, ±5%.

By the calculation function 105e, the processing circuitry 105 calculates an average of variation rates of the detection efficiency per set of hardware, such as a scintillator, a detector unit, a power supply unit, or a data transfer route, and, when the average of variation rates of the detection efficiency exceeds a given threshold in specific hardware part, the processing circuitry 105 determines that an abnormality occurs in the hardware part.

An embodiment in which normalization is performed by a combination of normalization with a radiation source at the time of manufacturing and the above-described single mode data measurement using self-radiation and crystal efficiency correction data is generated will be described. First of all, the background of normalization using normalization with a radiation source and single mode data measurement using self-radiation will be described briefly.

The histogram into which gamma ray events from radionuclides in the scintillator and a histogram based on gamma rays from a subject that is arranged in the PET gantry do not coincide perfectly. This results from the fact that, compared to the former case where it is possible to count scintillation light as a detection event similarly in all the detection elements, non-uniformity in the number of events occur between detection elements due to scattering in a detector chassis occurs in the latter case.

Accordingly, in each medical device according to the embodiment, normalization with a radiation source and crystal efficiency calculation are executed at the time of manufacturing and, in a medical setting, when the apparatus is executed, a pure variations in the detection efficiency that is obtained from collection without a radiation source is applied to correction data.

Figure 5:
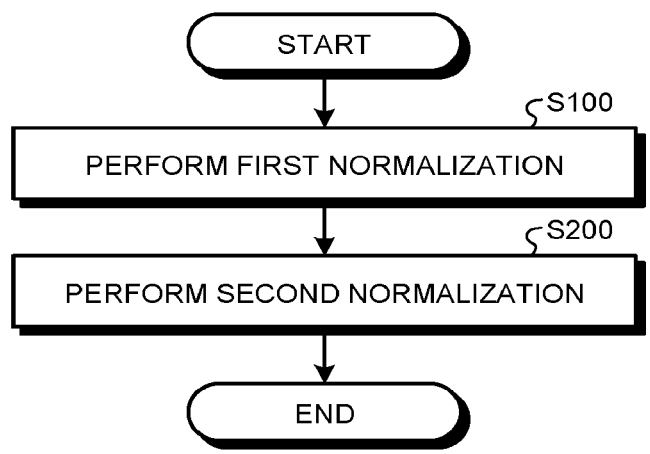
FIG. 5 is a flowchart illustrating a process performed by the nuclear medicine diagnosis apparatus according to the embodiment.

In other words, as illustrated in FIG. 5, first of all, at step S100, typically, the PET apparatus 100 performs first normalization at the time of manufacturing of the PET apparatus 100 or factory shipping.

Accordingly, it is possible to perform more accurate normalization considering geometric arrangement of the detectors in the gantry, or the like.

Figure 6:
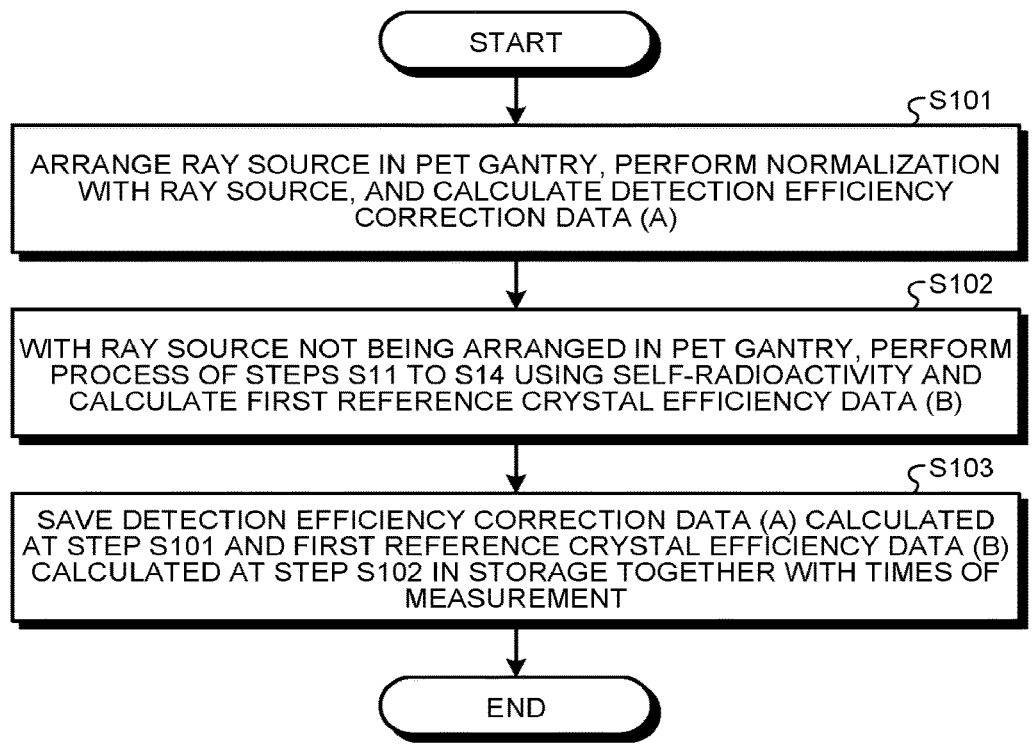
FIG. 6 is a flowchart illustrating a process of step S100 in FIG. 5 more in detail.
Figure 7:
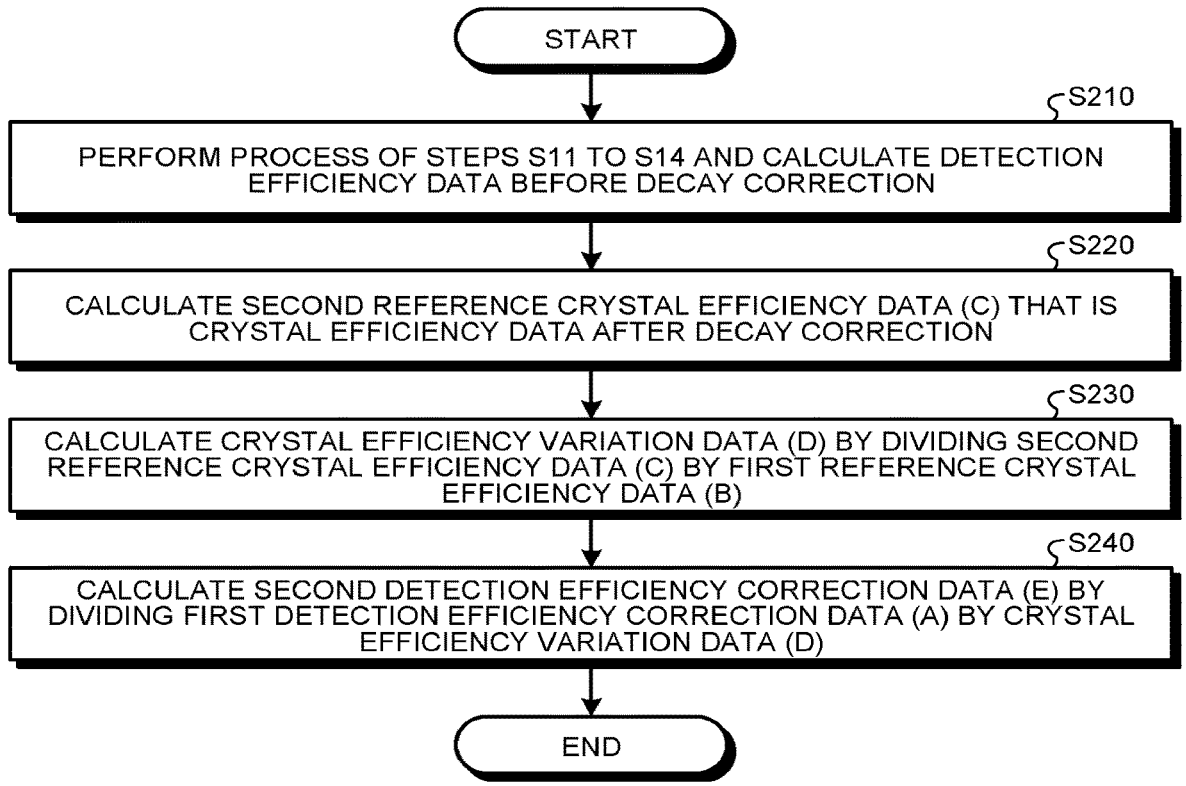
FIG. 7 is a flowchart illustrating a process of step S200 in FIG. 5 more in detail.

Details of the process of first normalization that is performed at step S100 are illustrated in FIG. 6 and step S100 in FIG. 5 corresponds to steps S100 to S103 in FIG. 6. At step S200, typically, for example, when the PET apparatus 100 is used in a medical setting, or the like, the PET apparatus 100 performs second normalization. Details of the process of the second normalization performed at step S200 are illustrated in FIG. 7 and step S200 in FIG. 5 corresponds to steps S210 to 240 in FIG. 7.

First of all, using FIG. 6, the process of the first normalization performed at step S100 will be described.

First of all, at step S101, the PET apparatus 100 arranges the radiation source in the gantry 10 and, using the external radiation source, performs normal normalization with a radiation source. The processing circuitry 105 acquires data on the normal normalization with a radiation source and, by the calculation function 105e, calculates crystal efficiency correction data (A) (first detection efficiency correction data). The crystal efficiency correction data (A) is data containing information of a crystal efficiency obtained by performing measurement with the radiation source being arranged in the gantry 10 at the time of manufacturing. In another example, the crystal efficiency correction data (A) is data obtained by a simulation. The crystal efficiency correction data (A) is, for example, correction data for absorbing and correcting the difference between Coincidence mode data and single mode data and the difference in geometrical arrangement of the radiation source on whether the radiation source is in the gantry or in the detector.

At step S101, by the calculation function 105e, the processing circuitry 105 may calculate the crystal efficiency correction data (A) by, instead of the process of performing the normal normalization using an external radiation source, generating a look-up table (LUT) by a simulation, such as a Monte Carlo simulation.

Subsequently, at step S102, the PET apparatus 100 performs the process from step S11 to step S14 in FIG. 4 using self-radiation with the radiation source not being arranged in the gantry 10 and, by the calculation function 105e, the processing circuitry 105 calculates first reference crystal efficiency data (B) (first detection efficiency data). The first reference crystal efficiency data (B) is crystal efficiency data that is obtained using self-radiation and is collected in, for example, the single mode at the time of manufacturing.

Subsequently, at step S103, the storage 130 stores the detection efficiency correction data (A) that is calculated at step S101 and the first reference crystal efficiency data (B) that is calculated at step S102 in the first storage 131 together with the times of measurement. In other words, the storage 130 stores the crystal efficiency correction data (A) (the first detection efficiency correction data) that is generated based on the external radiation source or a simulation and the first reference crystal efficiency data (B) (the first detection efficiency data) per scintillator that is calculated based on radiation emitted from the scintillator.

As described above, while the crystal efficiency correction data (A) (the first detection efficiency correction data) is data that is generated based on radiation that is emitted from the radiation source that is arranged in the gantry 10, the first reference crystal efficiency data (B) (the first detection efficiency data) and second reference crystal efficiency data (C) (second detection efficiency data) are data that is calculated based on data representing single photon detection events of radiation that is emitted from the scintillator. As described above, acquiring both the data that is generated based on radiation that is emitted from the radiation source arranged in the gantry 10 and the data representing single photon detection events of radiation that is emitted from the scintillator at the time of manufacturing makes it possible to correct the effect of geometrical arrangement of the detectors in the gantry 10, or the like, and accurately correct the crystal efficiency without using an external radiation source at times excluding manufacturing.

Subsequently, using FIG. 7, the process of the second normalization that is performed at step S200 will be described.

First of all, at step S210, the process from step S11 to step S14 in FIG. 4 is performed using self-radiation with the radiation source not being arranged in the gantry 10 in, for example, a medical setting, or the like, and, by the calculation function 105e, the processing circuitry 105 calculates detection efficiency data before decay correction that is crystal efficiency data obtained using self-radiation at the time of use of the PET apparatus 100. The process of step S102 and the process of step S210 are the same except for the difference of the aspect that, while step S210 is performed when the PET apparatus 100 is used in, for example, a medical setting, or the like, step S102 is performed at the time of manufacturing, factory shipping, or the like.

Subsequently, at step S220, by the calculation function 105e, the processing circuitry 105 performs the same process as that of step S20 and, based on the detection efficiency data before decay correction that is calculated at step S210, calculates second reference crystal efficiency data (C) that is crystal efficiency data after decay correction. The second reference crystal efficiency data (C) is crystal efficiency data that is collected at the time of use of the apparatus in a medical setting, or the like, that is obtained using self-radiation, and that is collected in, for example, the single mode. In other words, by the calculation function 105e, the processing circuitry 105 calculates the second detection efficiency data (C) per scintillator that is calculated based on radiation that is emitted from the scintillator.

Subsequently, at step S230, by the generation function 105b, the processing circuitry 105 divides the second reference crystal efficiency data (C) by the first reference crystal efficiency data (B), thereby calculating crystal efficiency variation data (D). The same data collection method is used for the second reference crystal efficiency data (C) and the first reference crystal efficiency data (B) and the second reference crystal efficiency data (C) and the first reference crystal efficiency data (B) only differ in the period of data collection, and the effect of self-decay of radionuclides has been corrected and thus the crystal efficiency variation data (D) represents an amount indicating how the crystal efficiency varies from the time of manufacturing when the first normalization is performed to the second normalization.

Subsequently, at step S240, by the generation function 105b, the processing circuitry 105 divides the first detection efficiency correction data (A) by the crystal efficiency variation data (D), thereby calculating the second detection efficiency correction data (E). The first detection efficiency correction data (A) is data of the crystal efficiency in the case where the radiation source is used and the crystal efficiency variation data (D) is an amount indicating how the crystal efficiency varies from the time of manufacturing to the time when the second normalization is performed. Accordingly, the second detection efficiency correction data (E) obtained through such a procedure serves, when the second normalization is executed, as data indicating a crystal efficiency in the case assuming that normalization is performed using the external radiation source. Accordingly, performing the process from step S210 to step S240 makes it possible to perform normalization as appropriate without using an external radiation source at times excluding manufacturing. As described above, by the generation function 105b, the processing circuitry 105 generates the second detection efficiency correction data (E) based on the first detection efficiency correction data (A), the first detection efficiency data (the first reference crystal efficiency data (B)), and the second detection efficiency data (the second reference crystal efficiency data (C)).

Note that the PET apparatus 100 is able to automatically execute the process of the second normalization at step S200. For example, by the calculating function 105e, the processing circuitry 105 may automatically execute the process of step S200 (in other words, the process of steps S210 to S240) during the idle time of the PET apparatus 100 and thus automatically execute correction of the crystal efficiency or automatically monitor the state of the PET apparatus 100.

In other words, the PET apparatus 100 automatically measures radiation that is emitted from the scintillators of which the detector 1 consists, for example, during the idle time of the PET apparatus 100. By the calculation function 105e, the processing circuitry 105 automatically calculates the second detection efficiency data based on radiation that is emitted from the scintillators and that is measured automatically. By the generation function 105b, the processing circuitry 105 automatically generates the second detection efficiency correction data based on the calculated second detection efficiency data.

In the case of such an embodiment, correction of the crystal efficiency is executed automatically, which enables the PET apparatus 100 to be maintenance-free.

As described above, according to the embodiment, because no radiation source is dealt with, it is possible to reduce worker radiation exposure in medical settings. Furthermore, variation in position in which a radiation source is set reduces in normalization (calibration of detection efficiency). Furthermore, variation in accuracy due to non-uniformity in distribution of isotopes in a radiation source also decreases.

In addition to this, in some embodiments, it is possible to perform normalization without requiring a manual work of setting or removal of a radiation source. Accordingly, by calculating a variation from a reference of crystal efficiency automatically in the idle time of the apparatus makes it possible to utilize the apparatus as an apparatus state monitoring system. Leading the monitoring result to update correction data enables a maintenance-free configuration.

In other words, according to at least one of the embodiments described above, it is possible to perform normalization while reducing worker radiation exposure or perform moralization accurately.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A nuclear medicine diagnosis apparatus, comprising:
a scintillator configured to emit self-radiation;
a memory storing (1) first detection efficiency correction data that is generated based on an external radiation source or a simulation, and (2) first detection efficiency data per scintillator that is calculated based on radiation that is emitted from the scintillator; and
processing circuitry configured to
calculate second detection efficiency data per scintillator based on radiation that is emitted from the scintillator, and
generate second detection efficiency correction data based on the stored first detection efficiency correction data, the stored first detection efficiency data, and the calculated second detection efficiency data,
wherein the processing circuitry is further configured to divide the second detection efficiency data by the first detection efficiency data to calculate crystal efficiency variation data, and divide the first detection efficiency correction data by the calculated crystal efficiency variation data, to calculate the second detection efficiency correction data.

2. The nuclear medicine diagnosis apparatus according to claim 1, wherein the scintillator is configured to emit gamma rays that are emitted from lutetium as the self-radiation.

3. The nuclear medicine diagnosis apparatus according to claim 1, wherein the first detection efficiency correction data stored in the memory is data generated based on radiation emitted from a radiation source arranged in a gantry; and
the first detection efficiency data and the second detection efficiency data are data calculated based on data representing single photon detection events of the radiation emitted from the scintillator.

4. The nuclear medicine diagnosis apparatus according to claim 1, wherein the processing circuitry is further configured to calculate a variation in a crystal efficiency based on radiation from the scintillator and, based on the calculated variation in the crystal efficiency, perform an abnormality sensing process.

5. The nuclear medicine diagnosis apparatus according to claim 1, wherein the processing circuitry is further configured to generate the first detection efficiency correction data by generating a look-up table by a Monte Carlo simulation.

6. The nuclear medicine diagnosis apparatus according to claim 1, wherein the nuclear medicine diagnosis apparatus is configured to automatically measure radiation emitted from the scintillator, and
the processing circuitry is further configured to
automatically calculate the second detection efficiency data based on radiation emitted from the scintillator and measured automatically, and
automatically generate the second detection efficiency correction data based on the calculated second detection efficiency data.

7. The nuclear medicine diagnosis apparatus according to claim 1, wherein the nuclear medicine diagnosis apparatus is configured to measure the radiation that is emitted from the scintillator in an idle time of the nuclear medicine diagnosis apparatus.

* * * * *